(12) United States Patent
Williams

(10) Patent No.: US 6,447,290 B1
(45) Date of Patent: Sep. 10, 2002

(54) PROTECTIVE ELEMENT FOR USE WITH DENTAL BRACES

(76) Inventor: Dan A. Williams, 18313 60th Ave. W., Lynnwood, WA (US) 98037

( * ) Notice: Subject to any disclaimer, the term of this patent is extended or adjusted under 35 U.S.C. 154(b) by 0 days.

(21) Appl. No.: 09/706,420

(22) Filed: Nov. 3, 2000

(51) Int. Cl.7 .................................................. A61C 3/00
(52) U.S. Cl. ............................................ 433/2; 433/22
(58) Field of Search ................................ 433/2, 22, 48

(56) References Cited

U.S. PATENT DOCUMENTS

| | | | | |
|---|---|---|---|---|
| 4,512,740 A | * | 4/1985 | Kurz | 433/22 |
| 4,559,013 A | * | 12/1985 | Amstutz et al. | 433/22 |
| 4,881,713 A | * | 11/1989 | Wise | 433/48 |
| 5,037,296 A | * | 8/1991 | Karwoski | 433/22 |
| 5,662,471 A | * | 9/1997 | Fogerty | 433/22 |
| 5,938,435 A | * | 8/1999 | Raspino, Jr. | 433/22 |
| 5,954,500 A | * | 9/1999 | Springs | 433/22 |

\* cited by examiner

*Primary Examiner*—Cary E. O'Connor
(74) *Attorney, Agent, or Firm*—Jensen & Puntigam, P.S.

(57) ABSTRACT

The protective element includes a flexible, cotton flannel base portion and a wax portion which impregnates the base portion to produce a combination article, wherein the wax portion is formulated so that the combination article is sufficiently flexible to prevent the wax portion from cracking away from the base portion at room temperature, and further such that the flexibility of the article increases sufficiently when the article is warmed by placement in the mouth to permit conforming application of the article to the dental appliance, and further such that the article remains in place against the dental appliance during use.

5 Claims, 3 Drawing Sheets

PROTECTIVE ELEMENT FOR USE WITH DENTAL BRACES

TECHNICAL FIELD

This invention relates generally to dental appliances, and more specifically concerns a protective element designed to be used with braces and other dental appliances.

BACKGROUND OF THE INVENTION

Braces or similar dental appliances typically limit or even eliminate certain activities of the user. These include the playing of certain musical instruments, such as woodwinds and brass, which are difficult to play properly with braces or other appliances, and which if played can result in injury to the mouth tissues of the user. Certain athletic activities, such as soccer and field hockey, are also usually limited or considered risky, again because of the possibility of injury to the mouth of the user.

Further, many people who use braces or other dental appliances are often unable to speak distinctly. Braces sometimes produce slurs or other undesirable speech patterns, which are accentuated when amplified. Hence, those people doing radio or other broadcast work are typically hindered by braces and/or other dental appliances.

Still further, irritations can occur in the user's mouth because of wires breaking or coming loose, or other failure of the appliance.

It should be understood that the above-described disadvantages could occur not only with braces but other dental appliances, including certain dentures and bridgework, as well. Accordingly, it would be desirable to have temporary (short-term) protection for such braces/appliances which would eliminate or reduce the above disadvantages to permit short-term activities such as sports and/or playing a musical instrument.

SUMMARY OF THE INVENTION

Accordingly, the invention is a protective element for use with dental appliances, comprising: a flexible, cloth base portion; and a wax portion which impregnates the base portion to produce a combined article, wherein the combined article is sufficiently flexible and pliable at room temperature to prevent the article from cracking away from the base layer, and wherein the flexibility and pliability of the combined article increases sufficiently by placing the article in the mouth or under warm water to permit convenient application of the article to dental appliances and subsequent adherence thereto during activities of the user involving the mouth.

BEST MODE FOR CARRYING OUT THE INVENTION

Figure 1:
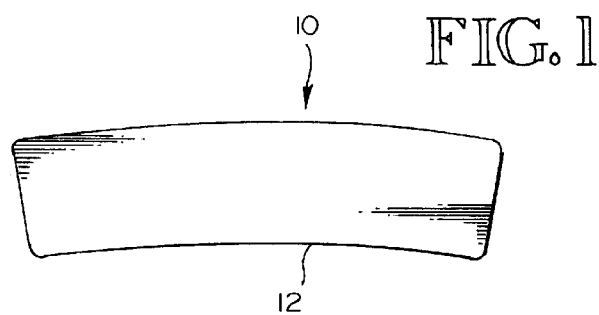
FIG. 1 is a top view of a sheet of the protective element of the present invention.

The purpose of the present invention is to provide a simple, easily applied protective element for short-term use on the exposed portion of braces or appliances. It is not designed to replace conventional mouth guards. The disclosed protective element is inexpensive, easy to apply and remains in place during temporary normal activities, such as athletic competition, playing musical instruments and other such activities. The element assists in preventing injury to the mouth tissues of the user during such activities.

The article of the present invention, shown generally at 10, comprises two parts. One part is a base layer 12. Base layer 12 is a fabric material; in the embodiment shown, it is 100% cotton flannel, having a slight nap on both sides. The weight of the material is four ounces per square yard. Such material is widely available. The structure of the material is such that it can be readily impregnated with a wax formulation. The material may, of course, be varied, as long as it accomplishes the objectives of the present invention. For instance, alternative materials include various cotton blends, as long as they permit impregnation with a wax formulation and give adequate strength to the completed article.

The second part of article 10 is a wax formula portion 14 which impregnates the cotton base layer 12. The wax portion 14 surrounds and encapsulates the cotton material base portion, so that the combination element 10 is thus substantially a unitary article.

The wax portion 14 in the embodiment shown is a formulation which includes four (4) parts of a refined, colorless paraffin wax, such as Moore & Munger Wax R-2838; one (1) part microcrystalline wax, such as Moore & Munger M-7356 or Paragon H800b; and one (1) part 100% corn oil. Pink food coloring can be added to give a desired shade, similar to mouth tissue. Other colors can, of course, be used to provide a contrasting or other desired color. Flavoring can be used as well. The above blend is used to produce the protective article.

The article is somewhat flexible at room temperature so that wax portion 14, which bonds to and impregnates the base layer 12, does not crack, peel or separate from the base layer. This is important to permit initial handling of the article without the article cracking or separating.

The formulation has the additional important characteristic of the melting point of the article being such that the article becomes more flexible and malleable upon exposure to the warm temperature of the mouth or warm water. This characteristic permits the article to readily conform to the contours of the braces or other dental appliance when applied by the user, and then to remain in place, somewhat flexibly, during normal activities of the user. The article thus remains sufficiently flexible during use that it does not crack or come off the braces. The user can then pursue (on a temporary or short-term basis) normal activities with the protective element in place, including light eating and drinking, as well as doing desired special activities, like playing musical instruments and engaging in athletic activities.

Figure 3A:
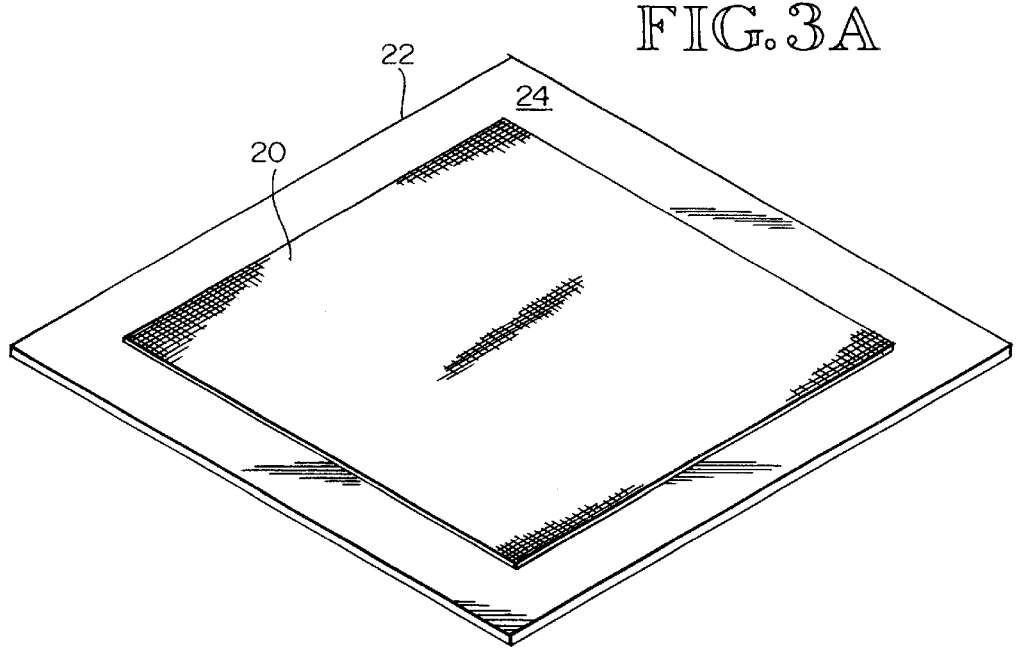
FIGS. 3A–3D show a series of process steps in the basic manufacture of the protective element of the present invention.

The steps in the basic manufacture of the article of the present invention are set forth in FIGS. 3A–3D. Referring to FIG. 3A, the base cotton material is first cut to a specific size, for example, 10 inches square. The material piece shown at 20 in FIG. 3A, which is the base layer of the article, is then positioned on a first aluminum alloy sheet 22, which in the embodiment shown is approximately 12 inches square or larger. The upper surface 24 of sheet 22 is polished and machined flat and should be at least ¼ inch thick. The first sheet 22 is preheated to a temperature of at least 140° F. before the material piece 20 is laid on it. Material piece 20 will be slightly smaller than the dimensions of sheet 22, so that the sheet extends beyond the edges of material piece 20. Material piece 20 should be laid flat on sheet 22, spread evenly, on the polished surface 24 and approximately centered.

Figure 3B:
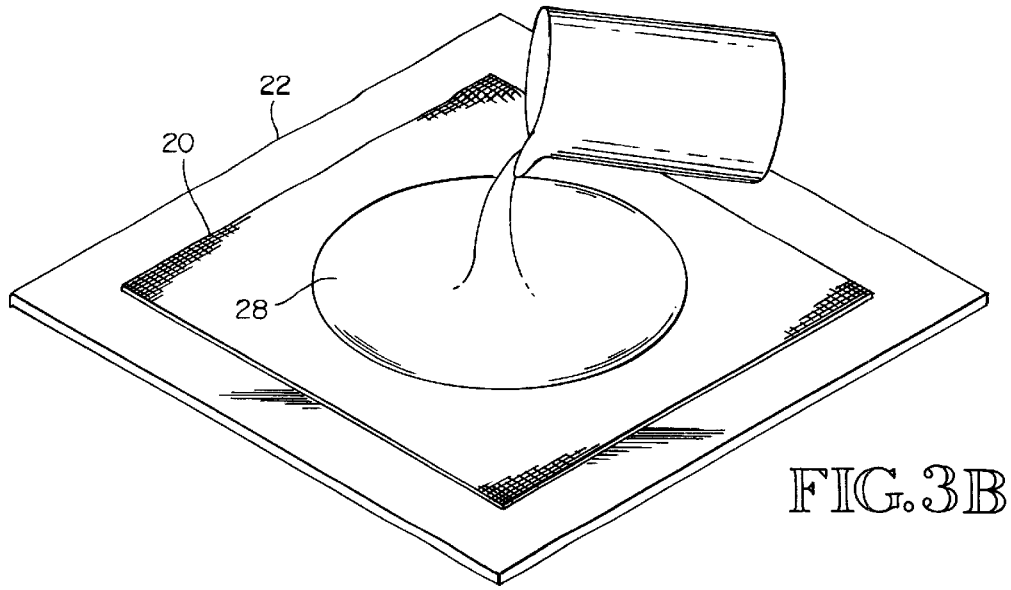
Figure 3C:
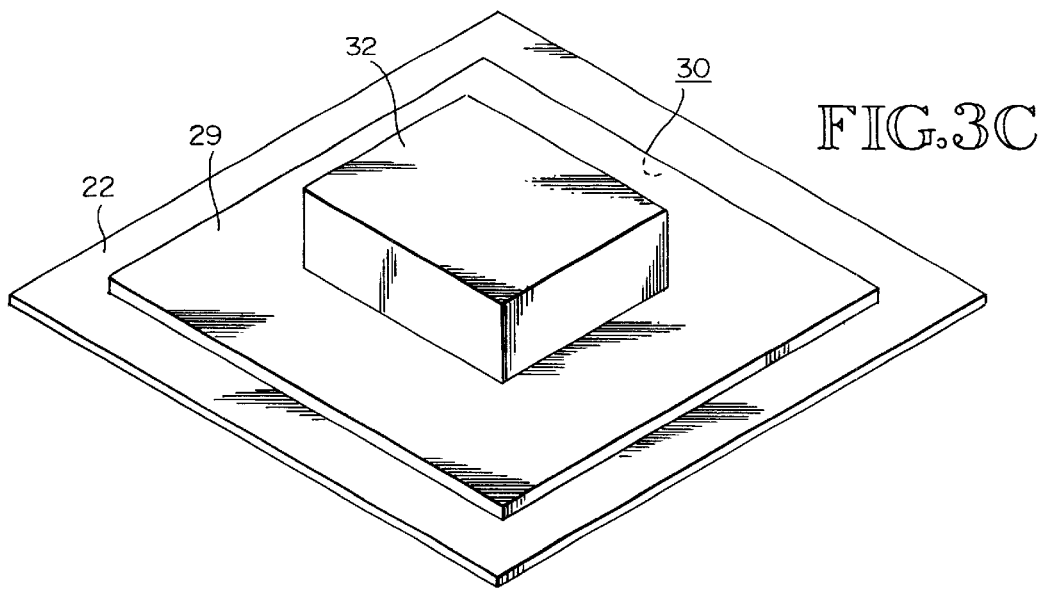

Referring now to FIG. 3B, the wax formulation discussed above, having been melted and mixed together, is poured over material piece 20, typically in the center of the material, as shown at 28. Enough wax is used to impregnate, i.e. saturate, material piece 20 over a substantial portion thereof. Referring now to FIG. 3C, a second sheet 29, which has also been heated to at least approximately 140° F., is positioned on top of the saturated material piece 20 with a polished surface 30 thereof adjacent the impregnated piece 20. Typically, a weight, shown representationally at 32, is positioned so as to provide a certain amount of pressure downwardly against the impregnated base material piece. In the embodiment shown, this weight is approximately 20 lbs, although this can be varied. As a result, any excess wax formula is forced outwardly from the center of sheet 20, producing a uniform thickness to the finished protective article.

Figure 2:
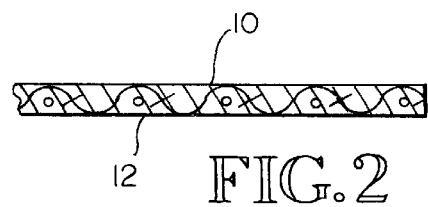
FIG. 2 is an edge view of the sheet of FIG. 1.
Figure 3D:
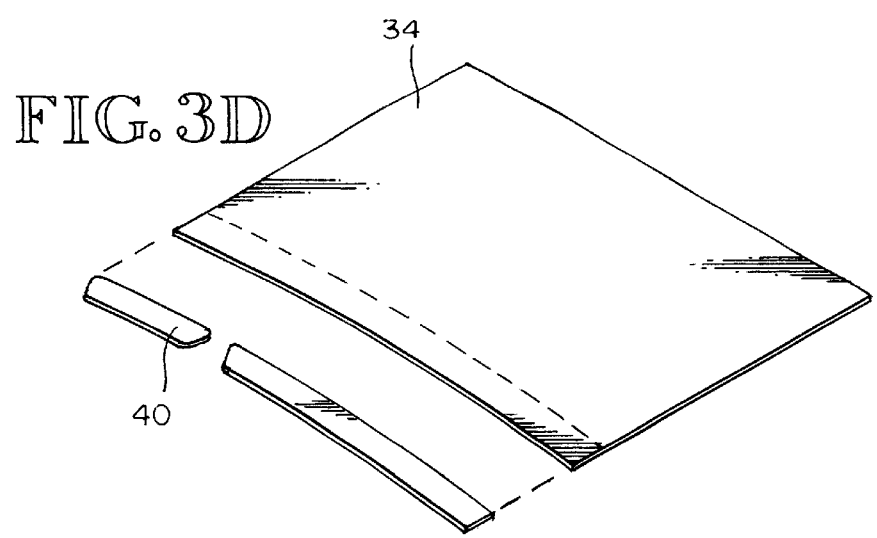

The impregnated material piece, between the two aluminum sheets 22 and 29, is allowed to cool until just slightly warm, at which point the upper sheet 29 is removed by lifting it up, exposing the pressed impregnated piece 34. The impregnated piece 34 is then removed from the lower sheet 22. As indicated above, the finished article is slightly flexible and pliable and does not break apart or peel away from the base cloth piece. The finished sheet 34 can then be cut into desired-sized pieces 40 and provided to the user (FIG. 3D). Typical dimensions are 70 mm×14 mm×1 mm, with a slight curve over the length of the piece. All corners of each piece are radiused, as shown in FIG. 3D and FIGS. 1 and 2.

Figure 4:
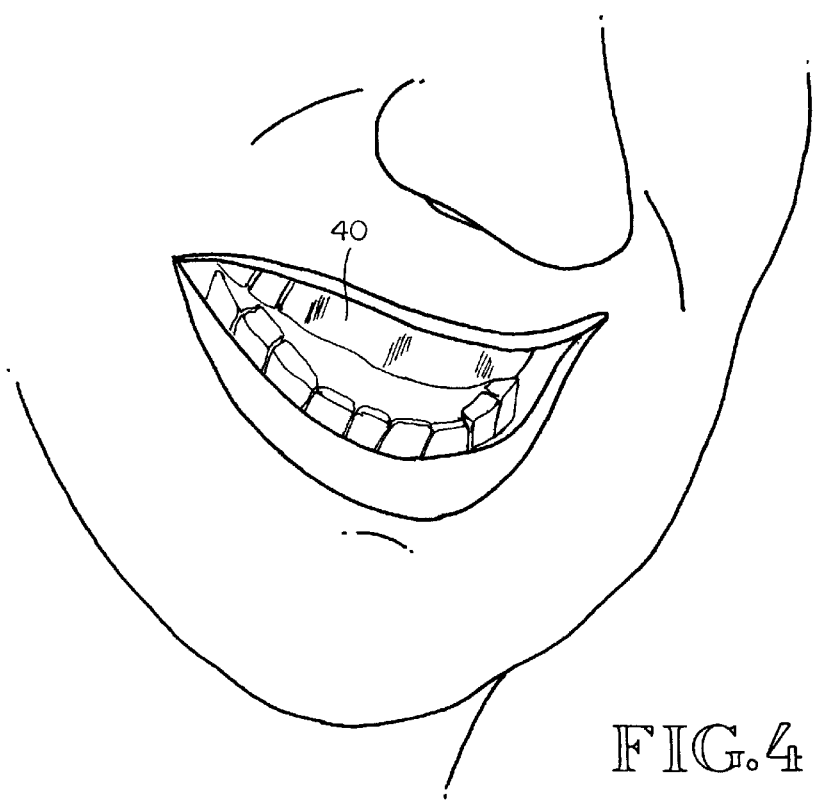
FIG. 4 shows the present invention in place on a user's upper teeth.

The user may trim the protective elements slightly to fit the braces or other dental appliance on which they will be used. An individual element is warmed in the mouth or under warm water until it becomes quite flexible and pliable. The protective element 40 is then positioned by the user over the braces or dental appliance, as shown in FIG. 4. The protective element is pressed slightly against the braces and positioned and molded into place by use of the tongue, lips and fingers.

With the protective element now in place, as shown in FIG. 4, normal activities in the short term are possible. It should be understood, however, that the protective element is not intended to replace conventional full mouth protective guards for use in various high contact activities, like, for instance, football. The design and construction of the protective element permits the various activities described above, including playing musical instruments and engaging in desired athletic activities, without dislodging or otherwise affecting the position of the protective element on the braces. The construction of the protective element is such that the element can be in place for extended periods of time, although it is still intended for temporary use. After a specific use, the element may be pulled off gently and either saved for its next use or discarded if worn out. It is in fact intended that the individual elements be used more than once, and they are designed to do so. Elements can be used for the upper or lower teeth or both (separately).

Accordingly, a protective element has been disclosed which is simple, inexpensive and reliable to use. It provides protection for the user's lips and tissues relative to braces and other dental appliances, and permits activities such as the use of musical instruments and certain athletic activities which would otherwise be difficult or painful for the individual to engage in.

Although a preferred embodiment has been disclosed for purposes of illustration, it should be understood that various changes, modifications, and substitutions may be incorporated in the embodiment without departing from the spirit of the invention just defined or defined by the claims that follow.

What is claimed is:

1. A protective element for dental appliances, comprising:

a flexible, cloth base portion; and a wax portion, which comprises four (4) parts paraffin wax, one (1) part microcrystalline wax, and one (1) part vegetable oil, impregnating the base portion to produce a combined article, wherein the combined article is sufficiently flexible and pliable at room temperature to prevent the article from cracking away from the base layer, and wherein the flexibility and pliability of the combined article increases sufficiently by placing the article in the mouth or under warm water to permit convenient application of the article to dental appliances and subsequent adherence thereto during activities of the user involving the mouth.

2. The protective element of claim 1, wherein the base portion is cotton flannel material.

3. The protective element of claim 1, wherein the wax portion includes pink food coloring to resemble the color of the mouth tissues.

4. The protective element of claim 1, wherein the element is shaped to cover a front portion of the dental appliance and is sufficiently thick to fit over and protect the mouth tissues of the user from the appliance.

5. The protective element of claim 1, wherein the dental appliance is dental braces.

* * * * *